United States Patent [19]

Clinton, deceased et al.

[11] 4,311,710

[45] Jan. 19, 1982

[54] ANTICOCCIDIAL FORMULATION AND METHOD

[75] Inventors: Albert J. Clinton, deceased, late of Indianapolis, Ind., by Cheryl L. Clinton, administrator; American Fletcher National Bank and Trust Company, special administrator, Indianapolis, Ind.

[73] Assignee: Eli Lilly and Company, Indianapolis, Ind.

[21] Appl. No.: 110,307

[22] Filed: Jan. 8, 1980

[51] Int. Cl.$^3$ ............................................ A61K 31/135
[52] U.S. Cl. .................................................. 424/330
[58] Field of Search ........................ 424/330; 260/571

[56] References Cited

FOREIGN PATENT DOCUMENTS 156  1/1979  European Pat. Off. .

*Primary Examiner*—Sam Rosen
*Attorney, Agent, or Firm*—Charles W. Ashbrook; Arthur R. Whale

[57] ABSTRACT

N-(Nitrophenyl)-polyfluoroalkoxybenzenamines are useful in the treatment of coccidial infections in animals.

17 Claims, No Drawings

ANTICOCCIDIAL FORMULATION AND METHOD

BACKGROUND OF THE INVENTION

European Pat. No. 156 discloses a group of benzenamines which are named as 2-anilino-3,5-dinitrobenzotrifluoride derivatives. The anilino ring can bear a haloalkoxy substituent. Such compounds are said to possess insecticidal, acaricidal, nematocidal, insect growth retardant, fungicidal and bactericidal activity. No mention is made that certain of the compounds might be useful in the treatment and control of coccidiosis.

I have now discovered that certain N-(nitrophenyl)-polyfluoroalkoxybenzenamines, including some of the compounds taught by the above noted reference, exhibit good anticoccidial activity. It therefore is an object of this invention to provide novel formulations of such compounds for use in treating coccidial infections in animals. It is a further object of the invention to provide a method for treating and controlling coccidial infections in animals utilizing such compounds.

SUMMARY OF THE INVENTION

This invention concerns a method of treatment of coccidiosis utilizing certain N-(nitrophenyl)-polyfluoroalkoxy benzenamines. The invention is more particularly directed to a method of treating coccidiosis in animals comprising administering an anticoccidial amount of a benzenamine of the formula

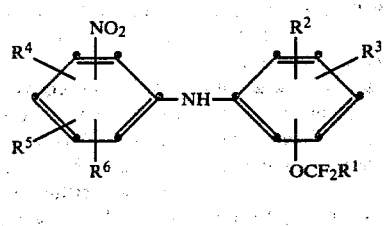

wherein:

$R^1$ is fluoro, difluoromethyl or trifluoromethyl;

$R^2$ and $R^3$ independently are hydrogen or halo;

$R^4$ is hydrogen, trifluoromethyl, cyano, $C_1$–$C_4$ alkyl, hydroxycarbonyl, or $C_1$–$C_4$ alkoxycarbonyl;

$R^5$ is hydrogen, halo, nitro, hydroxy, methoxy, or amino;

$R^6$ is hydrogen or nitro; and the physiologically-acceptable salts thereof.

Preferred methods utilize compounds of the above formula having one or more of the following characteristics:

1. $R^1$ is fluoro or difluoromethyl;
2. $R^2$ and $R^3$ are the same, and preferably are hydrogen;
3. $R^4$ is hydrogen, trifluoromethyl, cyano, $C_1$–$C_4$ alkyl, or hydroxycarbonyl;
4. $R^4$ is trifluoromethyl;
5. $R^5$ is nitro or halo, preferably chloro or bromo;
6. $R^6$ is nitro.

A further preferred method utilizes a compound of the formula

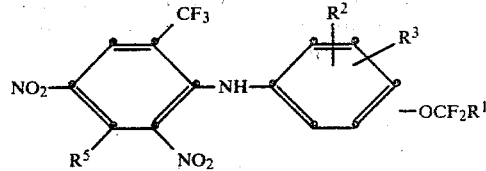

wherein $R^1$, $R^2$ and $R^3$ are as defined above, and $R^5$ is hydrogen or halo.

An especially preferred method according to this invention is a process for controlling or treating coccidiosis in poultry comprising orally administering to poultry a feedstuff comprising a benzenamine of the above formula and a carrier therefor.

An additional embodiment of this invention is a formulation useful in the treatment and control of coccidiosis in animals comprising an N-(nitrophenyl)polyfluoroalkoxybenzenamine of the above formula admixed with a suitable carrier, diluent or excipient therefor. A preferred formulation is a poultry feedstuff composition comprising a benzenamine of the above formula and a suitable carrier therefor.

DETAILED DESCRIPTION OF THE INVENTION $R^2$, $R^3$ and $R^5$ in the above formula include the groups referred to herein as "halo". The term bears its art-recognized meaning of fluoro, chloro, bromo and iodo. Preferred halo groups defined by $R^2$, $R^3$ and $R^5$ are chloro and bromo.

$R^4$ in the above formula includes $C_1$–$C_4$ alkyl groups, which are straight and branched chain alkyl groups having from one to four carbon atoms. Typical $C_1$–$C_4$ alkyl groups include methyl, ethyl, n-propyl, iso-propyl, n-butyl and tert.-butyl.

$R^4$ additionally defines a $C_1$–$C_4$ alkoxycarbonyl moiety, for instance methoxycarbonyl, ethoxycarbonyl, isopropoxycarbonyl, n-butoxycarbonyl, and related groups.

The N-nitrophenyl-polyfluoroalkoxybenzenamines comprehended by this invention can be prepared by any of several chemical processes. A preferred and commonly utilized process involves the condensation reaction of a substituted phenyl electrophilic agent with a phenylamine derivative. For example, a polyfluoroalkoxyphenyl electrophilic agent such as a phenyl halide can be condensed with a nitrophenylamine according to the following scheme:

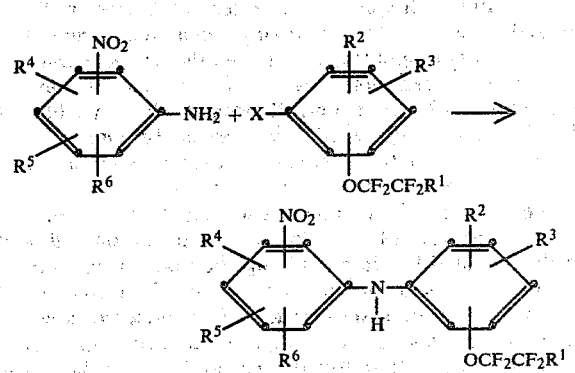

wherein $R^1$, $R^2$, $R_3$, $R^4$, $R^5$ and $R^6$ are as defined above, and X is a good leaving group such as halo, for instance chloro, bromo or iodo. A similar, yet alternative, process comprises condensing a nitrophenyl electrophilic agent with a polyfluoroalkoxyphenylamine according to the following scheme:

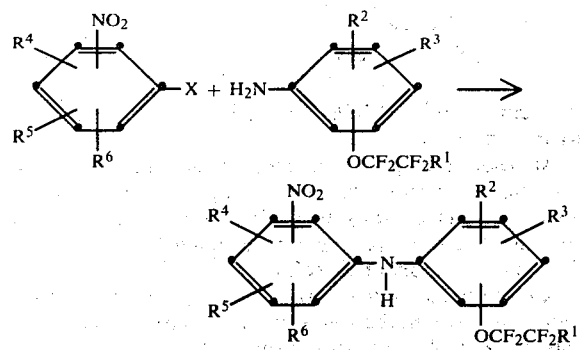

wherein $R^1$, $R^2$, $R^3$, $R^4$, $R^5$ and $R^6$ are as defined above, and X is a good leaving group such as halo.

According to the processes outlined above, a substituted phenyl electrophilic agent such as a trifluoromethoxyphenyl bromide or a tetra or pentafluoroethoxyphenyl chloride is mixed with about an equimolar quantity of a nitrophenylamine. The condensation reaction generally is carried out in an unreactive organic solvent and in the presence of a strong base. Commonly used unreactive organic solvents include amides, for instance dimethylformamide or hexamethylphosphortriamide; ethers such as tetrahydrofuran, diethyl ether, or dioxane; sulfoxides such as dimethyl sulfoxide; alcohols such as methanol or ethanol; and related solvents. Strong bases which may be utilized in the reaction include alkli metal hydrides, for instance sodium hydride or lithium hydride; amines such as triethylamine, pyridine, DBN (1,5-diazabicyclo [4.3.0]-non-5-ene) and DBU (1,5-diazabicyclo [5.4.0] undec-5-ene, carbonates such as potassium carbonate and sodium carbonate; alkoxides such as potassium tert.-butoxide, and the like.

The condensation reaction generally is carried out by first adding a phenylamine to a strong base in a suitable solvent. For instance, a phenylamine such as 3-(1,1,2,2-tetrafluoroethoxyphenyl)amine can be reacted with a base such as sodium hydride in a solvent such as dimethylformamide. The reactants can be employed in about equimolar quantities, or if desired an excess of base, for example about a 0.1 to about a 10 molar excess, can be utilized if desired. The phenylamine and the strong base generally are allowed to react for up to about 3 hours at a temperature of about $-30°$ to about $30°$ C., preferably about $0°$ to about $25°$ C. Following the initial reaction of the phenylamine and the strong base, the desired substituted phenyl electrophilic agent, for instance a compound such as 2,4-dinitro-6-trifluoromethylphenyl chloride, is added to the reaction mixture, and the reaction is permitted to continue for about 2 to about 48 hours at a temperature of about $0°$ to about $100°$ C.

The product of the condensation reaction is a compound to be utilized according to this invention and is readily isolated by simply adding the reaction mixture to an aqueous acid solution, for instance dilute aqueous hydrochloric acid or sulfuric acid. The desired product often precipitates out of the aqueous acid solution as a solid or an oil. Alternatively, the product may be extracted into a water immiscible organic solvent such as diethyl ether, ethyl acetate, dichloromethane, or the like. Removal of the organic solvent, for instance by evaporation under reduced pressure, then provides a compound of this invention. The product thus formed can be further purified if desired by any of several standard methods, including column chromatography over a solid support such as silica gel or the like, or crystallization from common solvents such as ethanol, benzene, skelly B, diethyl ether, acetone, and the like.

Certain benzenamines which are employed in the method provided by this invention can be prepared by modification of an existing benzenamine prepared as described above. For example, benzenamines bearing a carboxylic acid moiety, that is to say compounds of the above general formula wherein $R^4$ is hydroxycarbonyl, are readily esterified to provide benzenamines wherein $R^4$ is a $C_1-C_4$ alkoxy carbonyl group. Such conversion can be accomplished by standard esterification reactions. Methyl esters are often preferably prepared by simply reacting a free acid with diazomethane in a suitable solvent such as diethyl ether. Esterification can also be accomplished by condensing a benzenamine carboxylic acid with a $C_1-C_4$ alkanol in the presence of an acid, for instance sulfuric acid or the like. Alternatively, a benzenamine carboxylic acid can be converted to an acid halide, and the acid halide then can be condensed with a $C_1-C_4$ alkanol. For example, reaction of a benzenamine such as N-(2-nitro-4-hydroxycarbonylphenyl)-4-(1,1,2,2-tetrafluoroethoxy)benzenamine with oxalyl chloride affords N-(2-nitro-4-chlorocarbonylphenyl)-4-(1,1,2,2-tetrafluoroethoxy)benzenamine, which when reacted with an alkanol such as isopropanol affords N-(2-nitro-4-isopropoxycarbonylphenyl)-4-(1,1,2,2-tetrafluoroethoxy)benzenamine.

Benzenamines having the above formula wherein one or both of $R^2$ and $R^3$ are hydrogen can be halogenated by reaction with a halogenating agent in a suitable solvent. For instance, a compound such as N-(2,6-dinitro-4-trifluoromethyl)-3-(1,1,2,2-tetrafluoroethoxy)benzenamine can be reacted with about one equivalent, or an excess if desired, of bromine in the presence of a solvent such as dichloromethane or a mixture of acetic acid and water. Such reaction effects bromination to provide, for instance, N-(2,6-dinitro-4-trifluoromethyl)-2,4-dibromo-5-(1,1,2,2-tetrafluoromethoxy)benzenamine.

When desired, the above described halogenation reaction can be carried out utilizing less than one molar quantity of halogenating agent, thereby effecting monohalogenation instead of dihalogenation. The monohalogenated product can be further halogenated if desired with the same or a different halogenating agent. For instance a benzenamine such as N-(2,6-dinitro-4-trifluoromethylphenyl)-3-(1,1,2,2,2-pentafluoroethoxy)-benzenamine can be reacted with about a 0.5 molar amount of chlorine in dichloromethane at about $25°$ C. to give N-(2,6-dinitro-4-trifluoromethylphenyl)-2-chloro-3-(1,1,2,2,2-pentafluoroethoxy)benzenamine. The latter compound can be further halogenated, for instance by reaction with about a 0.5 to 1.0 molar amount of bromine in dichloromethane, to provide the corresponding dihalogenated derivative, for example N-(2,6-dinitro-4-trifluoromethylphenyl)-2-chloro-4-bromo-5-(1,1,2,2,2-pentafluoroethoxy)benzenamine.

The benzenamines contemplated herein are weakly acidic in nature by virtue of the activated proton attached to the amino nitrogen atom to which the two aromatic rings are attached. Because of this acidic nature, the benzenamines readily form physiologically-acceptable salts by reaction with any of a number of common inorganic and organic bases. The salts are in general solids and thus lend themselves to convenient purification by crystallization from common solvents such as ethanol, acetone, ethyl acetate, methyl ethyl ketone, and the like.

The salts provided herein are prepared by reaction of about equimolar quantities of a benzenamine and a base. Inorganic bases commonly employed to form salts of this invention include the alkali metal hydroxides such as sodium hydroxide and potassium hydroxide, as well as alkali metal amides such as lithium amide and potassium amide. Routinely used organic bases include alkali metal alkoxides such as potassium tert.-butoxide and sodium methoxide, as well as alkali metal amides such as lithium or potassium diisopropylamide.

When it is desired to regenerate the free amine from an addition salt, the salt is simply reacted with an acid such as hydrochloric acid or sulfuric acid. For example, reaction of the sodium salt of N-(2,4-dinitrophenyl)-3-(1,1,2,2-tetrafluoroethoxy)benzenamine with about one equivalent amount of hydrochloric acid converts the salt to a free amine to provide N-(2,4-dinitrophenyl)-3-(1,1,2,2-tetrafluoroethoxy)benzenamine.

Representative benzenamines to be employed in the method provided by this invention include the following:

N-(2,6-dinitro-4-trifluoromethylphenyl)-3-(1,1,2,2-tetrafluoroethoxy)benzenamine;
N-(2,6-dinitro-4-cyanophenyl)-2-(trifluoromethoxy)benzenamine;
N-(2,4-dinitro-6-trifluoromethylphenyl)-4-(1,1,2,2-tetrafluoroethoxy)benzenamine;
N-(2,4-dinitro-6-hydroxycarbonylphenyl)-3-(trifluoromethoxy)-4-chlorobenzenamine;
N-(2,4-dinitro-6-trifluoromethylphenyl)-4-(trifluoromethoxy)benzenamine;
N-(2-trifluoromethyl-4-nitrophenyl)-2-(1,1,2,2-tetrafluoroethoxy)benzenamine;
N-(3-trifluoromethyl-4-nitrophenyl)-3-(1,1,2,2-tetrafluoroethoxy)benzenamine;
N-(2,6-dinitro-4-ethoxycarbonylphenyl)-3-(1,1,2,2-tetrafluoroethoxy)-4,5-dichlorobenzenamine;
N-(2-nitrophenyl)-3-(trifluoromethoxy)benzenamine;
N-(2,4-dinitro-6-isopropyl)-2,6-dichloro-4-(1,1,2,2-tetrafluoroethoxy)benzenamine;
N-(2,4,6-trinitrophenyl)-3-(1,1,2,2-tetrafluoroethoxy)benzenamine;
N-(2,6-dinitro-3-bromo-4-trifluoromethylphenyl)-4-(1,1,2,2,2-pentafluoroethoxy)benzenamine;
N-(2-nitro-4-tert.-butylphenyl)-2,6-dibromo-4-(1,1,2,2-tetrafluoroethoxy)benzenamine;
N-(3,4-dinitrophenyl)-2-bromo-6-chloro-4-(1,1,2,2,2-pentafluoroethoxy)benzenamine;
N-(2,3,4-trinitro-5-methylphenyl)-2-(1,1,2,2-tetrafluoroethoxy)-3,5-dibromobenzenamine;
N-(2-nitro-4-ethoxycarbonylphenyl)-3-(1,1,2,2-tetrafluoroethoxy)benzenamine;
N-(2,4-dinitro-6-n-butylphenyl)-2,6-dichloro-3-(1,1,2,2-tetrafluoroethoxy)benzenamine;
N-(2,6-dinitro-6-hydroxycarbonylphenyl)-3-(1,1,2,2-tetrafluoroethoxy)benzenamine;
N-(2,4-dinitro-6-hydroxycarbonylphenyl)-2,6-difluoro-4-(trifluoromethoxy)benzenamine;
N-(2,4,6-trinitrophenyl)-2,4-diiodo-5-(1,1,2,2,2-pentafluoroethoxy)benzenamine;
Sodium N-(2-nitrophenyl)-3-(1,1,2,2,2-pentafluoroethoxy)benzenamide;
Potassium N-(2,6-dinitro-4-cyanophenyl)-2,6-dibromo-3-(1,1,2,2-tetrafluoroethoxy)benzenamide;
Lithium N-(2,4-dinitro-6-trifluoromethylphenyl)-3-(1,1,2,2-tetrafluoroethoxy)benzenamide;
Sodium N-(2,6-dinitro-4-trifluoromethylphenyl)-4-(trifluoromethoxy)benzenamide;
Lithium N-(2,4,6-trinitrophenyl)-2-(1,1,2,2-tetrafluoroethoxy)benzenamide;
N-(2-trifluoromethyl-5-chloro-4,6-dinitrophenyl)-4-(1,1,2,2-tetrafluoroethoxy)benzenamine;
N-(2,4-dinitro-6-hydroxycarbonylphenyl)-2,4-dibromo-5-(1,1,2,2-tetrafluoroethoxy)benzenamine;
Potassium N-(2,6-dinitro-4-trifluoromethyl)-3-bromo-4-(1,1,2,2-tetrafluoroethoxy)benzenamide;
Sodium N-(2-nitro-3-chloro-4-cyanophenyl)-2-(1,1,2,2-tetrafluoroethoxy)benzenamide;
N-(2,6-dinitro-4-trifluoromethylphenyl)-2,4-dichloro-5-(1,1,2,2,2-pentafluoroethoxy)benzenamine;
N-(2,4,6-trinitrophenyl)-3-(1,1,2,2,2-pentafluoroethoxy)benzenamine;
N-(2-trifluoromethyl-4-nitrophenyl)-3-(1,1,2,2,2-pentafluoroethoxy)benzenamine;
N-(2,4-dinitro-6-trifluoromethylphenyl)-4-(1,1,2,2,2-pentafluoroethoxy)benzenamine; and the like.

The detailed examples which follow illustrate the preparation of representative compounds useful in the method of the present invention. The examples are representative only and should not be construed as limiting in any respect.

EXAMPLE 1

N-(2,4-dinitro-6-trifluoromethylphenyl)-4-(1,1,2,2-tetrafluoroethoxy)benzenamine To a stirred solution of 1.0 g. of 4-(1,1,2,2-tetrafluoroethoxy)phenylamine in 50 ml. of ethanol containing 3.0 ml. of triethylamine were added in one portion 1.3 g. of 2,4-dinitro-6-trifluoromethylphenyl chloride. The reaction mixture was heated at reflux for sixteen hours following the addition. The reaction mixture then was added to 100 ml. of ice water containing about 10 ml. of hydrochloric acid. The precipitate which formed was collected and dissolved in diethyl ether. The ethereal solution was washed with water and dried, and the solvent was removed by evaporation under reduced pressure to provide 1.2 g. of N-(2,4-dinitro-6-trifluoromethylphenyl)-4-(1,1,2,2-tetrafluoroethoxy)benzenamine.

Yield 54.9% M.P. 105°–107° C. Analysis calculated for $C_{15}H_8F_7N_3O_5$— Theory: C, 40.65; H, 1.82; N, 9.48. Found: C, 40.89; H, 2.08; N, 9.66.

EXAMPLE 2

N-(2,6-dinitro-4-tert.-butylphenyl)-4-(1,1,2,2-tetrafluoroethoxy)benzenamine

A solution of 2.5 g. of 4-(1,1,2,2-tetrafluoroethoxy)phenylamine hydrochloride in 30 ml. of ethanol containing 5.0 ml. of triethylamine and 2.6 g. of 2,6-dinitro-4-tert.-butylphenyl chloride was stirred and heated at reflux for sixteen hours. The reaction mixture was then slowly added to 100 ml. of ice water containing 10 ml. of concentrated hydrochloric acid, and the aqueous mixture was stirred for thirty minutes. The oil which formed was collected and crystallized from skelly-B solvent and diethyl ether to give 2.4 g. of N-(2,6-dinitro-4-tert.-butylphenyl)-4-(1,1,2,2-tetrafluoroethoxy)benzenamine.

Yield 51.3% M.P. 142°–143° C.

Analysis calculated for $C_{18}H_{17}F_4N_3O_5$— Theory: C, 50.12; H, 3.97; N, 9.74. Found: C, 50.28; H, 4.02; N, 9.99.

EXAMPLES 3–12

Following the general procedure of Examples 1 and 2, the appropriate fluoroethoxyphenylamine was reacted with the appropriate nitrophenyl halide in the presence of triethylamine in ethanol to give the following benzenamines.

N-(2,6-dinitro-4-cyanophenyl)-4-(1,1,2,2-tetrafluoroethoxy)benzenamine.

Yield 89.3% M.P. 104°–106° C.

Analysis calculated for $C_{15}H_8F_4N_4O_5$— Theory: C, 45.01; H, 2.01; N, 14.00. Found: C, 45.29; H, 1.95; N, 14.04.

N-(2,6-dinitro-4-hydroxycarbonylphenyl)-4-(1,1,2,2-tetrafluoroethoxy)benzenamine.

Yield 74.6% M.P. 234°–236° C.

Analysis calculated for $C_{15}H_{11}N_3O_7$— Theory: C, 42.97; H, 2.16; N, 10.02. Found: C, 43.25; H, 2.36; N, 10.10.

N-(2,6-dinitro-3-chloro-4-trifluoromethylphenyl)-4-(1,1,2,2-tetrafluoroethoxy)benzenamine.

Yield 60.3% M.P. 127°–130° C.

Analysis calculated for $C_{15}H_7ClF_7N_3O_5$— Theory: C, 37.70; H, 1.47; N, 8.80. Found: C, 37.95; H, 1.53; N, 8.59.

N-(2,4-dinitro-6-hydroxycarbonylphenyl)-4-(1,1,2,2-tetrafluoroethoxy)benzenamine.

Yield 50.0% M.P. 192°–195° C.

Analysis calculated for $C_{15}H_8F_4N_3O_7$— Theory: C, 42.97; H, 2.16; N, 10.02. Found: C, 43.23; H, 2.30; N, 9.74.

N-(2,6-dinitro-4-tert.-butylphenyl)-3-(1,1,2,2-tetrafluoroethoxy)benzenamine.

M.P. 129°–131° C.

Analysis calculated for $C_{18}H_{17}F_4N_3O_5$— Theory: C, 50.12; H, 3.97; N, 9.74. Found: C, 50.02; H, 3.89; N, 9.48.

N-(2,6-dinitro-4-trifluoromethylphenyl)-3-(1,1,2,2-tetrafluoroethoxy)benzenamine. (oil)

Analysis calculated for $C_{15}H_8F_7N_3O_5$— Theory: C, 40.65; H, 1.82; N, 9.48. Found: C, 40.91; H, 1.84; N, 9.24.

N-(2,4-dinitro-6-trifluoromethylphenyl)-3-(1,1,2,2-tetrafluoroethoxy)benzenamine.

M.P. 74°–76° C.

Analysis calculated for $C_{15}H_7F_7N_3O_5$— Theory: C, 40.56; H, 1.82; N, 9.48. Found: C, 40.87; H, 2.02; N, 9.49.

N-(2,6-dinitro-4-trifluoromethylphenyl)-4-(1,1,2,2-tetrafluoroethoxy)benzenamine.

Yield 83.5% M.P. 102°–105° C.

Analysis calculated for $C_{15}H_8F_7N_3O_5$— Theory: C, 40.65; H, 1.82; N, 9.48. Found: C, 40.82; H, 1.79; N, 9.63.

N-(2,4,6-trinitrophenyl)-4-(1,1,2,2-tetrafluoroethoxy)benzenamine.

M.P. 141°–142° C.

Analysis calculated for $C_{14}H_8N_4O_7$— Theory: C, 40.01; H, 1.92; N, 13.33. Found: C, 40.17; H, 2.04; N, 13.09.

N-(2,4,6-trinitrophenyl)-3-(1,1,2,2-tetrafluoroethoxy)benzenamine.

M.P. 128°–129° C.

Analysis calculated for $C_{14}H_8N_4O_7$— Theory: C, 40.01; H, 1.92; N, 13.33. Found: C, 40.14; H, 1.99; N, 13.44.

EXAMPLE 13

N-(2-trifluoromethyl-4-nitrophenyl)-3-(1,1,2,2-tetrafluoroethoxy)benzenamine

Two grams of a 50% suspension of sodium hydride in mineral oil were washed several times with pentane, and then suspended in 25 ml. of N,N-dimethylformamide. To the stirred mixture were added in one portion 3.8 g. of 3-(1,1,2,2-tetrafluoroethoxy)phenylamine. The reaction mixture was stirred at ambient temperature for thirty minutes, and then 4.5 g. of 2-trifluoromethyl-4-nitrophenylchloride were added dropwise over five minutes to the reaction mixture. The mixture was stirred for three hours at room temperature, and then added slowly to 100 ml. of dilute hydrochloric acid solution. An oil which precipitated was collected, dissolved in diethyl ether, and chromatographed over silica gel. After collecting the fractions shown by thin layer chromatography to contain a single product and evaporating the solvent therefrom, there were recovered, as an oil, 2.0 g. of N-(2-trifluoromethyl-4-nitrophenyl)-3-(1,1,2,2-tetrafluoroethoxy)benzenamine.

Analysis calculated for $C_{15}H_9F_7N_3O_3$— Theory: C, 45.24; H, 2.28; N, 7.03. Found: C, 45.03; H, 2.24; N, 7.09.

EXAMPLES 14–17

N-(2,6-dinitro-4-trifluoromethylphenyl)-2-(1,1,2,2-tetrafluoroethoxy)benzenamine Analysis calculated for $C_{15}H_8F_7N_3O_5$— Theory: C, 40.65; H, 1.82; N, 9.48. Found: C, 40.85; H, 1.80; N, 9.48.

N-(2,4-dinitro-6-hydroxycarbonylphenyl)-2-(1,1,2,2-tetrafluoroethoxy)benzenamine Analysis calculated for $C_{15}H_9F_4N_3O_7$— Theory: C, 43.08; H, 1.93; N, 10.05. Found: C, 43.27; H, 2.01; N, 9.81.

N-(2,4,6-trinitrophenyl)-2-(1,1,2,2-tetrafluoroethoxy)benzenamine.

M.P. 114°–115° C.

Aalysis calculated for $C_{14}H_8F_4N_4O_7$— Theory: C, 40.01; H, 1.92; N, 13.33. Found: C, 39.88; H, 1.99; N, 13.62.

N-(2,4-dinitro-6-tert.-butylphenyl)-4-(1,1,2,2-tetrafluoroethoxy)benzenamine.

M.P. 98°–101° C.

Analysis calculated for $C_{18}H_{17}F_4N_3O_5$— Theory: C, 50.12; H, 3.97; N, 9.74. Found: C, 50.24; H, 4.01; N, 9.86.

EXAMPLE 18

N-(2,4-dinitro-6-trifluoromethylphenyl)-2,6-dichloro-4-(1,1,2,2-tetrafluoroethoxy)benzenamine A solution of 0.9 g. of N-(2,4-dinitro-6-trifluoromethylphenyl)-4-(1,1,2,2-tetrafluoroethoxy)benzenamine in 15 ml. of glacial acetic acid containing 3 ml. of water was stirred at room temperature while excess chlorine was bubbled therethrough. The reaction mixture was stirred for thirty minutes, and then the solvent was removed by evaporation under reduced pressure to provide an oil. The oil was dissolved in 100 ml. of diethyl ether, and the ethereal solution was dried, treated with decolorizing charcoal, and filtered. Removal of the solvent by evaporation provided a yellow oil, which when crystallized from skelly-B afforded N-(2,4-dinitro-6-trifluoromethylphenyl)-2,6-dichloro-4-(1,1,2,2-tetrafluoroethoxy)benzenamine.

M.P. 80°–82° C.

Analysis calculated for $C_{15}H_6Cl_2F_7N_3O_5$— Theory: C, 35.18; H, 1.18; N, 8.21. Found: C, 35.48; H, 1.31; N, 8.50.

EXAMPLE 19

N-(2,4-dinitro-6-trifluoromethylphenyl)-4-(1,1,2,2-tetrafluoroethoxy)benzenamine was reacted with bromine in acetic acid and water according to the method of Example 18 to provide
N-(2,4-dinitro-6-trifluoromethylphenyl)-2,6-dibromo-4-(1,1,2,2-tetrafluoroethoxy)benzenamine.
M.P. 92°–93° C.

Analysis calculated for $C_{15}H_6Br_2F_7N_3O_5$— Theory: C, 29.98; H, 1.01; N, 6.99. Found: C, 30.12; H, 1.05; N, 7.17.

EXAMPLE 20

N-(2,4,6-trinitrophenyl)-2,4-dibromo-5-(1,1,2,2-tetrafluoroethoxy)benzenamine

To a stirred solution of 1.7 g. of N-(2,4,6-trinitrophenyl)-3-(1,1,2,2-tetrafluoroethoxy)benzenamine in 20 ml. of dichloromethane were added in one portion 1.5 ml. of bromine. The reaction mixture was heated at reflux for sixteen hours, and then 1.0 ml. of bromine was added. The mixture was refluxed for an additional two hours, and then cooled to room temperature. The precipitate which formed was collected by filtration to provide 1.4 g. of N-(2,4,6-trinitrophenyl)-2,4-dibromo-5-(1,1,2,2-tetrafluoroethoxy)benzenamine.
M.P. 201°–203° C.

Analysis calculated for $C_{14}H_5Br_2F_4N_4O_7$— Theory: C, 29.09; H, 1.05; N, 9.69. Found: C, 29.35; H, 0.96; N, 9.81.

EXAMPLES 21–23

Various benzenamines were halogenated in dichloromethane by the procedure of Example 20 to give the following halo substituted benzenamines:

N-(2,6-dinitro-4-trifluoromethylphenyl)-2,4-dichloro-5-(1,1,2,2-tetrafluoroethoxy)benzenamine.
M.P. 142°–143° C.

Analysis calculated for $C_{15}H_6Cl_2F_7N_3O_5$— Theory: C, 35.18; H, 1.18; N, 8.21. Found: C, 35.48; H, 1.19; N, 8.12.

N-(2,6-dinitro-4-trifluoromethylphenyl)-2,4-dibromo-5-(1,1,2,2-tetrafluoroethoxy)benzenamine.
M.P. 161°–163° C.

Analysis calculated for $C_{15}H_6Br_2F_7N_3O_6$— Theory: C, 29.98; H, 1.01; N, 6.99. Found: C, 30.04; H, 1.18; N, 7.14.

N-(2,4-dinitro-6-trifluoromethylphenyl)-2,4-dibromo-5-(1,1,2,2-tetrafluoroethoxy)benzenamine.
(oil)

Analysis calculated for $C_{15}H_6Br_2F_7N_3O_5$— Theory: C, 36.94; H, 1.77; N, 9.24. Found: C, 37.24; H, 2.05; N, 9.55.

EXAMPLE 24

The following benzenamine is prepared according to the procedure set out in European Pat. No. 156.
N-(2,4-dinitro-6-trifluoromethylphenyl)-4-(trifluoromethoxy)benzenamine.

To a boiling suspension of 27.0 g. of 2,4-dinitro-6-trifluoromethylphenyl chloride and 17.7 g. of 4-trifluoromethoxyphenylamine in 200 ml. of water were added portion-wise over thirty minutes 9.3 g. of sodium bicarbonate. Following complete addition of the sodium bicarbonate, the reaction mixture was heated at reflux for two hours, and then cooled to room temperature and stirred for about sixteen hours. The precipitate which had formed was collected by filtration, washed with petroleum ether, and dried to provide 36.8 g. of N-(2,4-dinitro-6-trifluoromethylphenyl)-4-(trifluoromethoxy)benzenamine.
M.P. 104° C.

Similarly prepared were the following N-nitrophenyl-trifluoromethoxybenzenamines:

N-(2,4-dinitro-6-trifluoromethylphenyl)-2-chloro-4-trifluoromethoxybenzenamine;

N-(2,4-dinitro-6-trifluoromethylphenyl)-3-chloro-4-trifluoromethoxybenzenamine;

N-(2,4-dinitro-6-trifluoromethylphenyl)-3-trifluoromethoxybenzenamine; and the like.

The benzenamines described above and defined by the above general formula are utilized according to this invention in the treatment and control of coccidiosis in animals. The method of this invention may be practiced for the prophylactic control of coccidiosis, for instance by the routine and continued administration to an animal susceptible to coccidiosis of an effective dose of a benzenamine, as well as for the therapeutic treatment of coccidiosis in animals so infected. The compounds can be formulated for convenient administration to animals by any of a number of routes, including the oral, intramuscular, intravenous, subcutaneous and related routes. The compounds are preferably formulated for systemic administration to animals such as bovine. As already noted, a preferred method according to the invention comprises treating poultry for coccidial infections. The benzenamines defined above are especially useful in treating and in aiding in the prevention of coccidiosis in poultry caused by *Eimeria necatrix, E. tenella, E. acervulina, E. brunetti, E. mivati,* and *E. maxima.* The method of this invention is ideally suited to the prevention of coccidiosis in broiler chickens.

For treatment of poultry according to this invention, the benzenamines are preferably formulated for oral administration, for instance as a feedstuff, by addition to the normal daily feed ration of the animals. Ideally, the benzenamine anticoccidial agent will be uniformly dispersed throughout a finished animal feed mixture. Such medicated feed mixture is then administered ad lib. to animals such as chickens and turkeys. The normal concentration of benzenamine to be employed in a feedstuff will be from about 20 grams per ton to about 500 grams per ton, and more preferably about 100 g/T to about 300 g/T. Poultry will routinely consume about 5 to about 250 grams of such feedstuff per day, depending upon size and age of the bird.

Any of a number of poultry feedstuffs can be utilized as a suitable carrier or diluent for the benzenamines defined above. Typical feedstuffs include the following:

| Broiler Starter | |
|---|---|
| Ingredients | Percent |
| Corn, Yellow, Ground | 50.0 |
| Soybean Oil Meal, Solvent Extracted, Dehulled (50%) | 30.9 |
| Animal Fat | 6.5 |
| Fish Meal with Solubles (60%) | 5.0 |
| Corn Distillers Dried Solubles | 4.0 |
| Dicalcium Phosphate, Feed Grade | 1.8 |
| Calcium Carbonate (Ground Limestone) | 0.8 |
| Vitamin Premix TK-01 (1.03)[1] | 0.5 |
| Salt (NaCl) | 0.3 |

Broiler Starter -continued

| Ingredients | Percent |
|---|---|
| Trace Mineral Premix TK-01 (1.02)[2] | 0.1 |
| Methionine Hydroxy Analog | 0.1 |
| Total | 100.0 |

Broiler Grower

| Ingredients | Percent |
|---|---|
| Corn, Yellow, Ground | 57.7 |
| Soybean Meal, Solvent, Extracted, Dehulled (50%) | 31.7 |
| Animal Fat (Beef tallow) | 6.0 |
| Dicalcium Phosphate, Feed Grade | 2.7 |
| Calcium Carbonate (Ground Limestone) | 0.9 |
| Vitamin Premix TK-01 (1.03)[1] | 0.5 |
| Salt (NaCl) | 0.2 |
| Methionine Hydroxy Analog | 0.2 |
| Trace Mineral Premix TK-01 (1.02)[2] | 0.1 |
| Total | 100.0 |

Chick Starter, Light Breeds

| Ingredients | Percent |
|---|---|
| Corn, Yellow, Ground | 56.3 |
| Soybean Meal, Solvent Extracted, Dehulled (50%) | 17.9 |
| Wheat Middlings | 10.0 |
| Corn Distillers Dried Solubles | 5.0 |
| Fish Meal with Solubles | 5.0 |
| Alfalfa Meal, Dehydrated (17%) | 2.5 |
| Dicalcium Phosphate, Feed Grade | 1.3 |
| Calcium Carbonate | 0.9 |
| Vitamin Premix[1] | 0.5 |
| Salt (NaCl) | 0.3 |
| Methionine Hydroxy Analog | 0.2 |
| Trace Mineral Premix[2] | 0.1 |
| Total | 100.0 |

Pullet Grower

| Ingredients | Percent |
|---|---|
| Corn, Yellow, Ground | 73.5 |
| Soybean Meal, Solvent Extracted, Dehulled (50%) | 21.9 |
| Dicalcium Phosphate, Feed Grade | 2.5 |
| Calcium Carbonate | 1.0 |
| Vitamin Premix[1] | 0.5 |
| Salt (NaCl) | 0.3 |
| Methionine Hydroxy Analog | 0.2 |
| Trace Mineral Premix[2] | 0.1 |
| Total | 100.0 |

Pullet Developer

| Ingredients | Percent |
|---|---|
| Corn, Yellow, Ground | 67.5 |
| Oats, Ground Whole | 15.0 |
| Soybean Meal, Solvent Extracted, Dehulled (50%) | 13.4 |
| Dicalcium Phosphate, Feed Grade | 2.1 |
| Calcium Carbonate | 1.0 |
| Vitamin Premix[1] | 0.5 |
| Methionine Hydroxy Analog | 0.3 |
| Salt (NaCl) | 0.2 |
| Trace Mineral Premix[2] | 0.1 |
| Total | 100.0 |

Turkey Starter

| Ingredients | Percent |
|---|---|
| Soybean Meal, Solvent Extracted, Dehulled | 40.7 |
| Corn, Yellow, Ground | 39.7 |
| Fish Meal with Solubles | 5.0 |
| Beef Tallow | 5.0 |
| Corn Distillers Dried Solubles | 2.5 |
| Alfalfa Meal, Dehydrated (17%) | 2.5 |
| Dicalcium Phosphate, Feed Grade | 2.5 |
| Calcium Carbonate | 1.2 |
| Vitamin Premix[1] | 0.5 |
| Salt (NaCl) | 0.2 |
| Trace Mineral Premix[2] | 0.1 |
| Methionine Hydroxy Analog | 0.1 |
| Total | 100.0 |

Turkey Finisher

| Ingredients | Percent |
|---|---|
| Corn, Yellow, Ground | 71.2 |
| Soybean Meal, Solvent Extracted, Dehulled (50%) | 9.9 |
| Corn Distillers Dried Solubles | 5.0 |
| Alfalfa Meal, Dehydrated (17%) | 5.0 |
| Animal Fat | 3.0 |
| Fish Meal with Solubles | 2.5 |
| Dicalcium Phosphate, Feed Grade | 1.7 |
| Calcium Carbonate | 0.5 |
| Vitamin Premix[1] | 0.5 |
| Salt (NaCl) | 0.4 |
| Methionine Hydroxy Analog | 0.2 |
| Trace Mineral Premix[2] | 0.1 |
| Total | 100.0 |

[1]Vitamin premix provides 3000 IU of vitamin A, 900 ICU of vitamin D, 40 mg. of vitamin E, 0.7 mg. of vitamin K, 1000 mg. of choline, 70 mg. of niacin, 4 mg. of pantothenic acid, 4 mg. of riboflavin, 0.10 mg. of vitamin $B_{12}$, 0.10 mg. of biotin and 125 mg. of ethoxyquin per kg. of complete feed.
[2]Trace mineral premix provides 75 mg. of manganese, 50 mg. of zinc, 25 mg. of iron and 1 mg. of iodine per kg. of complete feed.

A benzenamine anticoccidial agent can be admixed with any such poultry feedstuffs so that the final feedstuff contains about 20 to about 500 grams of benzenamine per ton of feedstuff. For example, about 300 g. of a compound such as N-(2,4-dinitro-6-trifluoromethylphenyl)-4-(trifluoromethoxy)benzenamine can be added to about one ton of the above-noted Broiler Grower mixture for use according to this invention. Similarly, about 200 to about 300 g. of N-(2-trifluoromethyl-5-chloro-4,6-dinitrophenyl)-4-(1,1,2,2-tetrafluoroethoxy)-benzenamine can be admixed to uniformity with about one ton of the above-described Turkey Finisher for administration to turkeys pursuant to the method of this invention.

The benzenamines defined above can alternatively be formulated as a feedstuff pre-mix. For example, a benzenamine can be admixed with a substantially inert carrier such as ground rice hulls, soybean meal, wheat middlings, fermentation mycelia and the like. Nutritive carriers such as cereals can also be utilized. Such mixture of carrier and benzenamine anticoccidiostat will preferably contain about 5 to about 90 percent by weight of the benzenamine anticoccidial agent, and more preferably about 20 to about 70 percent by weight. Such pre-mix formulation is then mixed with a normal feed ration at a rate so that the active ingredient is present in about 20 to about 500 grams per ton of final feed ration.

Still another formulation which can be utilized according to this invention comprises a benzenamine of the above formula substantially dissolved in drinking water, for example in the drinking water of poultry such as chickens and turkeys. For such formulations, it is occasionally preferred to utilize a physiologically-acceptable salt such as the sodium or potassium salt, which compounds generally are substantially water soluble. For such formulation, it is often convenient to prepare water-soluble powders or dispersible powders comprising a benzenamine admixed with carriers such as dextrose, sucrose, dimethyl sulfoxide, or other suitable diluent. Typically, the benzenamine will be present in such forms in about 0.01 to about 30 percent by weight. Such powder or liquid formulations are conveniently added to the poultry drinking water at the site of administration.

The anticoccidial activity of the N-(nitrophenyl)-polyfluoroalkoxybenzenamines defined by the above formula has been determined in standard in vivo tests in chickens. A typical evaluation was conducted as follows:

one-week-old broiler chicks were alloted to five-bird cages and were fed a medicated or control ration, typically for one day, prior to infection with oocysts of a coccidiosis-causing organism. The chicks were maintained on their respective rations for a period of time, typically seven days. Generally, there were from three to six replicates per treatment. Anticoccidial efficacy was typically determined by the lesion scores, but other measures of efficacy were employed in many of the tests. In determining lesion scores, the birds were sacrificed and the severity of lesions scored on a 0-4 scale, with lesion-free birds scored as 0, extremely severe infections scored as 4, and intermediate degrees of infection scored as 1, 2, or 3. The scores of all birds which received a given treatment were averaged.

Table I below presents the results for the evaluation of N-(2,4-dinitro-6-trifluoromethylphenyl)4-(1,1,2,2-tetrafluoroethoxy)benzenamine. The results are a statistical analysis of intestinal lesion scores of broiler cockerels utilizing the Duncans Multiple Range Test (P<0.05) and Gebhardts algorithm for unequal sample size. The data is reported with superscript letters, and those data not followed by a common letter are significantly different. The animals were inoculated with strains of *Eimeria acervulina* (strain 59) and *Eimeria maxima* (strain F.S. 177).

TABLE I

| Treatment | Dose (ppm) | Intestinal Lesion Scores Replicates | Mean |
|---|---|---|---|
| Infected controls (no medication) | | 3 | 4.93$^c$ |
| N-(2,4-dinitro-6-trifluoromethyl-phenyl)-4-(1,1,2,2-tetrafluoroethoxy)-benzenamine | 10 | 3 | 3.00$^b$ |
| | 20 | 3 | 0.20$^a$ |
| | 30 | 3 | 0.00$^a$ |
| | 50 | 3 | 0.00$^a$ |

A similar evaluation was carried out to compare a benzeneamine of the invention with the anticoccidial agent known generically as monensin. Intestinal and cecal lesion scores were assigned to broiler cockerels inoculated with *Eimeria acervulina* (strain 59), *Eimeria tenella* (strain 155) and *Eimeria maxima* (strain F.S. 177). The results are presented in Table II.

TABLE II

| Treatment | Dose (ppm) | Intestinal Replicates | Intestinal Mean | Cecal Replicates | Cecal Mean |
|---|---|---|---|---|---|
| Infected control (no treatment) | | 2 | 5.60 | 2 | 3.55 |
| Monensin | 25 | 2 | 4.50 | 2 | 3.50 |
| | 50 | 2 | 0.90 | 2 | 1.73 |
| | 100 | 3 | 0.00 | 3 | 0.00 |
| N-(2,4-dinitro-6-trifluoro-methylphenyl)-4-(1,1,2,2-tetrafluoro-ethoxy)benzenamine | 8 | 2 | 6.00 | 2 | 3.75 |
| | 15 | 2 | 1.87 | 2 | 3.30 |
| | 30 | 3 | 0.20 | 3 | 1.73 |

I claim:

1. A method for treating coccidiosis in animals comprising administering to an animal an anticoccidial amount of a benzenamine of the formula

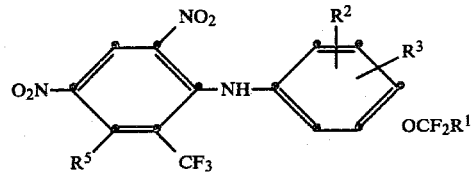

wherein:
$R^1$ is fluoro, difluoromethyl or trifluoromethyl;
$R^2$ and $R^3$ independently are hydrogen or halo;
$R^5$ is hydrogen or halo;
and the physiologically acceptable salts thereof.

2. The method of claim 1 wherein in the compound administered, $R^1$ is fluoro or difluoromethyl.

3. The method of claim 1 wherein in the compound administered, $R^2$ and $R^3$ both are halo or hydrogen.

4. The method of claim 3 wherein the compound administered, $R^2$ and $R^3$ both are hydrogen.

5. The method of claim 1 wherein the animal species treated is poultry.

6. The method of claim 5 wherein in the compound administered, $R^1$ is fluoro or difluoromethyl.

7. The method of claim 5 wherein in the compound administered, $R^2$ and $R^3$ are both hydrogen or halo.

8. The method of claim 7 wherein in the compound administered, $R^2$ and $R^3$ both are hydrogen.

9. The method of claim 5 wherein in the compound administered, $R^5$ is chloro or bromo.

10. The method of claim 5 wherein in the compound administered, $R^5$ is hydrogen.

11. An anticoccidial formulation comprising a poultry feedstuff and an effective amount of an anticoccidial benzenamine of the formula

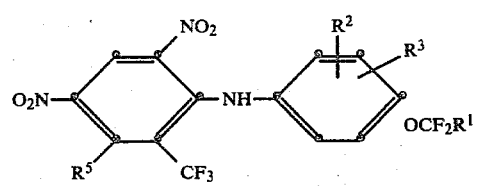

wherein:
$R^1$ is fluoro, difluoromethyl or trifluoromethyl;

$R^2$ and $R^3$ independently are hydrogen or halo;

$R^5$ is hydrogen or halo;

and the physiologically acceptable salts thereof.

12. The formulation of claim 11 wherein in the active ingredient, $R^1$ is fluoro or difluoromethyl.

13. The formulation of claim 11 wherein in the active ingredient, $R^2$ and $R^3$ are the same.

14. The formulation of claim 13 wherein in the active ingredient, $R^2$ and $R^3$ both are hydrogen.

15. The formulation of claim 11 wherein in the active ingredient, $R^5$ is chloro or bromo.

16. The formulation of claim 11 wherein in the active ingredient, $R^5$ is hydrogen.

17. The anticoccidial feedstuff of claim 11 wherein the active ingredient is N-(2,4-dinitro-6-trifluoromethylphenyl)-4-(1,1,2,2-tetrafluoroethoxy)benzenamine.